United States Patent [19]

Chakrabarti et al.

[11] Patent Number: 4,486,591
[45] Date of Patent: Dec. 4, 1984

[54] 4-SUBSTITUTED-1-(3-[2-AMINOANILINO]-1-PYRAZOLE-4-CARBONYL)PIPERAZINE

[75] Inventors: Jiban K. Chakrabarti, Camberley; Terrence M. Hotten, Farnborough, both of England

[73] Assignee: Lilly Industries Limited, London, England

[21] Appl. No.: 426,580

[22] Filed: Sep. 29, 1982

Related U.S. Application Data

[62] Division of Ser. No. 193,200, Oct. 2, 1980, Pat. No. 4,404,137.

[30] Foreign Application Priority Data

Oct. 16, 1979 [GB] United Kingdom ............... 7935846

[51] Int. Cl.³ ........................................... C07D 403/06
[52] U.S. Cl. ............................. 544/371; 260/239.3 T
[58] Field of Search ........................................ 544/371

[56] References Cited

U.S. PATENT DOCUMENTS

| | | | |
|---|---|---|---|
| 3,450,694 | 6/1969 | Swett et al. | 260/239.3 T |
| 3,660,380 | 5/1972 | Schmidt et al. | 260/239.3 |
| 3,743,734 | 7/1973 | Schmidt et al. | |
| 3,758,479 | 10/1973 | Schmutz et al. | 269/268 |
| 3,761,481 | 10/1973 | Nakanishi et al. | 260/268 |
| 3,951,981 | 4/1976 | Safir | 260/268 |
| 3,953,430 | 4/1976 | Safir | 260/239.3 |
| 4,115,568 | 9/1978 | Chakrabarti et al. | 424/250 |
| 4,115,574 | 9/1978 | Chakrabarti et al. | 424/250 |
| 4,172,831 | 10/1979 | Chakrabarti et al. | 260/239.3 |
| 4,404,137 | 9/1983 | Chakrabarti et al. | 260/239.3 T |

FOREIGN PATENT DOCUMENTS

| | | | |
|---|---|---|---|
| 3016 | 7/1979 | European Pat. Off. | 260/243.3 |
| 2707270 | 8/1978 | Fed. Rep. of Germany | 548/378 |

OTHER PUBLICATIONS

Rajappa et al., Indian J. Chem., 1976, 14B, 394–396.
Rajappa et al., CA85:177301e, (1976).
Schneider et al., CA80:14969m, (1974).
Plescia et al., CA92: 6514s, (1980).

Primary Examiner—Donald G. Daus
Assistant Examiner—S. A. Gibson
Attorney, Agent, or Firm—Karen B. Dow; Arthur R. Whale

[57] ABSTRACT

Compounds are described of the formula

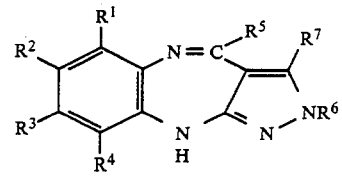

or an acid addition salt thereof;

in which $R^1$, $R^2$, $R^3$ and $R^4$ independently represent hydrogen, $C_{1-4}$ alkyl, $C_{2-4}$ alkenyl, $C_{3-7}$ cycloalkyl, $C_{3-7}$ cycloalkyl $C_{1-4}$ alkyl, halogen, $C_{1-4}$ haloalkyl, $C_{1-4}$ alkanoyl, nitro, amino, $C_{2-4}$ acylamino, cyano, hydroxyl, $C_{1-4}$ alkoxy, $C_{1-4}$ alkylthio, $C_{1-4}$ haloalkoxy or a group of the formula $-SO_2N(R^8)_2$, $-SO_2R^8$ or $-SO_3R^8$ where $R^8$ is $C_{1-4}$ alkyl, $C_{1-4}$ haloalkyl or optionally substituted phenyl; in which $R^5$ is a group of the formula

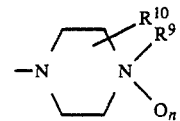

where $R^9$ is hydrogen, $C_{1-4}$ alkyl, $C_{3-7}$ cycloalkyl, $C_{3-7}$ cycloalkyl $C_{1-4}$ alkyl, $C_{1-4}$ haloalkyl, $C_{2-4}$ alkenyl, $C_{1-4}$ alkanoyl, benzyl, cyano or optionally substituted phenyl, where $R^{10}$ is hydrogen, $C_{1-4}$ alkyl or optionally substituted phenyl and where n is 0 or 1; in which $R^6$ is hydrogen, $C_{1-10}$ alkyl, $C_{3-7}$ cycloalkyl, $C_{3-7}$ cycloalkyl $C_{1-4}$ alkyl, $C_{1-4}$ haloalkyl, benzyl, $C_{1-6}$ alkanoyl, $C_{1-4}$ carbalkoxy or benzoyl; and in which $R^7$ is one of the values of $R^6$ or halogen, nitro, cyano, amino or $C_{1-4}$ acylamino. The compounds are active as pharmaceuticals and particularly in the treatment of disorders of the central nervous system.

1 Claim, No Drawings

4-SUBSTITUTED-1-(3-[2-AMINOANILINO]-1-PYRAZOLE-4-CARBONYL)PIPERAZINE

This application is a division of application Ser. No. 193,200 filed 10/2/80 now U.S. Pat. No. 4,404,137.

This invention relates to novel compounds, process for preparing them and their use as pharmaceuticals.

Various tricyclic compounds with pharmaceutical properties have already been investigated and these have been mainly of the type that comprise two benzene nuclei. We have now discovered a new group of compounds having the following basic structure

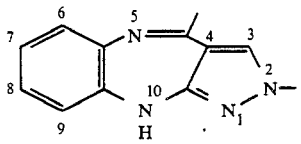

The compounds of the invention are of the following formula (I)

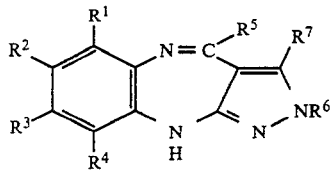

or an acid addition salt thereof;
in which $R^1$, $R^2$, $R^3$ and $R^4$ independently represent hydrogen, $C_{1-4}$ alkyl, $C_{2-4}$ alkenyl, $C_{3-7}$ cycloalkyl, $C_{3-7}$ cycloalkyl $C_{1-4}$ alkyl, halogen, $C_{1-4}$ haloalkyl, $C_{1-4}$ alkanoyl, nitro, amino, $C_{2-4}$ acylamino, cyano, hydroxyl, $C_{1-4}$ alkoxy, $C_{1-4}$ alkylthio, $C_{1-4}$ haloalkoxy or a group of the formula $-SO_2N(R^8)_2$, $-SO_2R^8$ or $-SO_3R^8$ where $R^8$ is $C_{1-4}$ alkyl, $C_{1-4}$ haloalkyl or optionally substituted phenyl; in which $R^5$ is a group of the formula

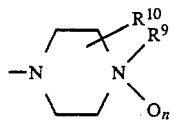

where $R^9$ is hydrogen, $C_{1-4}$ alkyl, $C_{3-7}$ cycloalkyl, $C_{3-7}$ cycloalkyl $C_{1-4}$ alkyl, $C_{1-4}$ haloalkyl, $C_{2-4}$ alkenyl, $C_{1-4}$ alkanoyl, benzyl, cyano or optionally substituted phenyl, where $R^{10}$ is hydrogen, $C_{1-4}$ alkyl or optionally substituted phenyl and where n is 0 or 1; in which $R^6$ is hydrogen, $C_{1-10}$ alkyl, $C_{3-7}$ cycloalkyl, $C_{3-7}$ cycloalkyl $C_{1-4}$ alkyl, $C_{1-4}$ haloalkyl, benzyl, $C_{1-6}$ alkanoyl, $C_{1-4}$ carbalkoxy or benzoyl; and in which $R^7$ is one of the values of $R^6$ or halogen, nitro, cyano, amino or $C_{1-4}$ acylamino.

Compounds of formula (I) have been found to possess useful biological properties and the invention includes a compound of formula (I) for use as a pharmaceutical and especially for use in the treatment of disorders of the central nervous system.

A particular group of compounds of formula (I) is one in which $R^1$, $R^2$ and $R^3$ independently represent hydrogen, $C_{1-4}$ alkyl, $C_{2-4}$ alkenyl, halogen, $C_{1-4}$ haloalkyl, nitro, $C_{1-4}$ alkoxy, $C_{1-4}$ haloalkoxy, $C_{1-4}$ alkylthio, $C_{1-4}$ haloalkylsulphonyl or phenylsulphonyl, $R^4$ is hydrogen, $R^6$ is hydrogen, $C_{1-6}$ alkyl, $C_{3-7}$ cycloalkyl, $C_{3-7}$ cycloalkyl $C_{1-4}$ alkyl or benzyl, $R^7$ is hydrogen or $C_{1-4}$ alkyl, $R^9$ is hydrogen, $C_{1-4}$ alkyl, $C_{3-7}$ cycloalkyl, $C_{3-7}$ cycloalkyl $C_{1-4}$ alkyl or benzyl, and $R^{10}$ is hydrogen or $C_{1-4}$ alkyl.

A preferred group of compounds is one of the following formula (II)

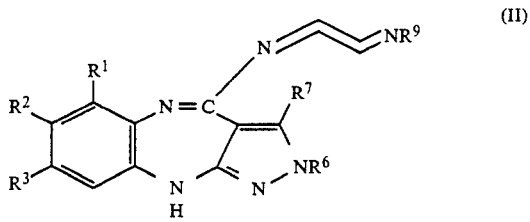

or an acid addition salt thereof; in which $R^1$, $R^2$ and $R^3$ independently represent hydrogen, $C_{1-4}$ alkyl, $C_{2-4}$ alkenyl, halogen, $C_{1-4}$ haloalkyl, nitro, $C_{1-4}$ alkoxy, $C_{1-4}$ alkylthio or phenylsulphonyl, $R^6$ is hydrogen, $C_{1-10}$ alkyl, $C_{3-7}$ cycloalkyl, $C_{3-7}$ cycloalkyl $C_{1-4}$ alkyl or benzyl, $R^7$ is hydrogen or $C_{1-10}$ alkyl and $R^9$ is hydrogen, $C_{1-4}$ alkyl, $C_{3-7}$ cycloalkyl, $C_{3-7}$ cycloalkyl $C_{1-4}$ alkyl or benzyl.

A preferred group of compounds of formula (II) is one in which $R^1$, $R^2$ and $R^3$ independently represent hydrogen, halogen or $C_{1-4}$ haloalkyl, $R^6$ is $C_{1-6}$ alkyl, $C_{3-7}$ cycloalkyl or $C_{3-7}$ cycloalkyl $C_{1-4}$ alkyl, $R^7$ is hydrogen and $R^9$ is hydrogen, $C_{1-4}$ alkyl, $C_{3-7}$ cycloalkyl $C_{1-4}$ alkyl or benzyl, the compounds in which $R^9$ is hydrogen being useful as intermediates in the preparation of preferred compounds.

Within the scope of compounds defined in formula (II) there can be listed compounds of especial interest, namely, those having one or more of the following features (a) $R^2$ is a halogen substituent, such as fluorine, chlorine or bromine, and $R^1$ and $R^3$ are hydrogen.

(b) $R^2$ and $R^3$ both represent halogen, especially fluorine or chlorine and $R^1$ is hydrogen.

(c) $R^3$ is halogen, especially fluorine, and $R^1$ and $R^2$ are hydrogen.

(d) $R^6$ is $C_{1-4}$ alkyl, especially methyl or ethyl (e) $R^7$ is hydrogen.

(f) $R^9$ is methyl

Specific examples of preferred compounds include
7-Bromo-2,10-dihydro-2-methyl-4-(4-methyl-1-piperazinyl)pyrazolo [3,4-b][1,5]benzodiazepine
7-Chloro-2-ethyl-2,10-dihydro-4-(4-methyl-1-piperazinyl)pyrazolo[3,4-b][1,5]benzodiazpine
7-Chloro-2,10-dihydro-2-methyl-4-(4-methyl-1-piperazinyl)pyrazolo[3,4-b][1,5]benzodiazepine
7,8-Dichloro-2,10-dihydro-2-methyl-4-(4-methyl-1-piperazinyl)pyrazolo[3,4-b][1,5]benzodiazepine
7-Fluoro-2-ethyl-2,10-dihydro-4-(4-methyl-1-piperazinyl)pyrazolo[3,4-b][1,5]benzodiazepine
7-Fluoro-2,10-dihydro-2-methyl-4-(4-methyl-1-piperazinyl)pyrazolo[3,4-b][1,5]benzodiazepine
8-Fluoro-2,10-dihydro-2-methyl-4-(4-methyl-1-piperazinyl)pyrazolo[3,4-b][1,5]benzodiazepine In the above general formulae, the term "$C_{1-10}$ alkyl" means a straight or branched chain alkyl group containing 1 to 10 carbon atoms and is especially, for example, methyl, ethyl, isopropyl, propyl, butyl, sec.butyl, isobutyl, tert, butyl, pentyl and hexyl. A preferred alkyl group is "$C_{1-4}$ alkyl". The term "$C_{1-4}$ haloalkyl" means any such alkyl group substituted by one or more, preferably three halogen atoms, and is especially trifluoromethyl. The terms "$C_{1-4}$ alkoxy" and "$C_{1-4}$ alkylthio" mean any $C_{1-4}$ alkyl group attached through an oxygen or sulphur atom to a ring atom and "$C_{1-4}$ haloalkoxy" means a $C_{1-4}$ alkoxy group substituted by one or more, preferably three halogen atoms and is especially trifluoromethoxy. The term "$C_{1-4}$ carbalkoxy" means a $C_{1-4}$ alkoxy group attached via a carbonyl group to a ring atom. "$C_{1-4}$ Alkanoyl" includes the formyl group and groups of the formula $R^{11}CO$ where $R^{11}$ is $C_{1-4}$ alkyl. The term "$C_{2-4}$ alkenyl" refers to groups such as vinyl, allyl and butanyl. The term "amino" indicates a group of formula —$NH_2$ and also substituted amino groups such as mono-$C_{1-4}$ alkylamino and di-$C_{1-4}$ alkylamino groups. The term "$C_{2-4}$ acylamino" means an amino group substituted by a $C_{2-4}$ acyl group especially acetyl. "$C_{3-7}$ Cycloalkyl" means a saturated ring having 3 to 7 carbon atoms in the ring such as cyclopropyl cyclobutyl, cyclopentyl, cyclohexyl or cycloheptyl, which can, in the group "$C_{3-7}$ cycloalkyl $C_{1-4}$ alkyl", be attached to the ring via an alkyl chain having 1 to 4 carbon atoms. The term "optionally substituted phenyl" means, a phenyl group which is unsubstituted or substituted by one or more groups, for example, halogen, $C_{1-4}$ haloalkyl, $C_{1-4}$ alkyl $C_{1-4}$ alkoxy or nitro. Specific examples of such substituents include chlorine, trifluoromethyl, methyl and methoxy.

As indicated above, the compounds of the invention are useful both in their free base and acid addition salt forms. The acid addition salts are preferably the pharmaceutically acceptable, non-toxic addition salts with suitable acids, such as those with inorganic acids, for example hydrochloric, hydrobromic, nitric, sulphuric or phosphoric acids, or with organic acids, such as organic carboxylic acids, for example, glycollic, maleic, hydroxymaleic, fumaric, malic, tartaric, citric or lactic acid, or organic sulphonic acids for example methane sulphonic, ethane sulphonic, 2-hydroxyethane sulphonic, toluene-p-sulphonic or naphthalene-2-sulphonic acid. Apart from pharmaceutically acceptable acid addition salts, other salts are also included within the scope of acid addition salts such as, for example, those with picric or oxalic acid, since they may serve as intermediates in the purification of the compounds or in the preparation of other, for example, pharmaceutically acceptable, acid addition salts, or are useful for identification, characterization or purification of the bases.

According to a further aspect of the invention there is provided a process for producing a compound of formula (I) or an acid addition salt thereof, which comprises (a) reacting an amine of formula $R^5H$ with a compound of formula (III)

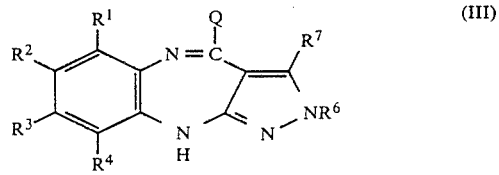

(III)

where Q represents a radical capable of being split off with the hydrogen atom of the amine $R^5H$, optionally followed when $R^6$ or $R^9$ is hydrogen by reaction with a compound of the formula $R^6X$ or $R^9X$ respectively, X being a leaving group, and optionally followed when n is o by oxidation, or (b) ring-closing a compound of formula (IV)

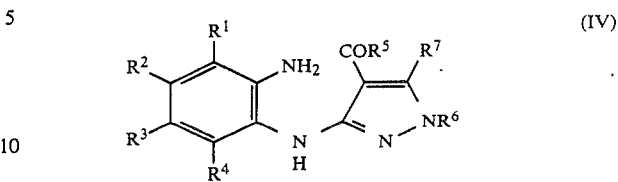

(IV)

optionally followed when $R^6$ or $R^9$ is hydrogen by reaction with a compound of the formula $R^6X$ or $R^9X$ respectively, X being a leaving group, and optionally followed when n is o by oxidation.

The above processes are of a general type previously described in the literature (see standard treatises for references to acylation, alkylation, oxidation and ring closure) and suitable Q and X radicals and appropriate reaction conditions can be readily chosen.

It may be mentioned, for example, that in reaction (a) the radical Q can be hydroxyl, thiol, an alkoxy or alkylthio group containing 1 to 4 carbon atoms, for example a methoxy or methylthio group, a halogen atom, especially a chlorine atom, an amino group or a mono- or dialkyl-substituted amino group, each alkyl substituent containing 1 to 4 carbon atoms. Preferably, Q is hydroxyl, thiol, $C_{1-4}$ alkoxy, $C_{1-4}$ alkylthio, halogen or amino and it is especially preferred that Q is hydroxyl, thiol or amino ($NH_2$). When Q is hydroxyl or thiol, the intermediates of formula (III) exist predominantly in their amide and thioamide forms:

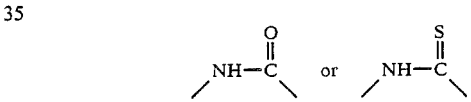

and when Q is amino the intermediates of formula (III) may also exist in the imino form:

When Q is hydroxyl, and the compound of formula (III) is an amide, reaction (a) can be accomplished in the presence of titanium tetrachloride which has the ability to react with the amine of formula $R^5H$ to form a metal amine complex. Other metal chlorides such as those of zirconium, hafnium or vanadium may also be employed. The reaction is preferably carried out in the presence of an acid binding agent such as a tertiary amine, for example, triethylamine. Alternatively, the reaction can be carried out using excess of the amine of formula $R^5H$ to act as an acid-binding agent. A suitable organic solvent such as toluene or chlorobenzene can be used as reaction medium, although it has been found that the use of anisole is particularly desirable, at least as a co-solvent, in view of its abiility to form a soluble complex with $TiCl_4$.

If desired, elevated temperatures, for example up to 200° C., can be used to expedite the reaction and a preferred temperature range for carrying out the reaction is from 100° C. to 150° C.

The amidines of formula (III) (Q is NH$_2$), can be in a salt form for example as the hydrochloride, and they can be similarly reacted with amines of formula R$^5$H, optionally diluted with a solvent such as anisole, dimethylformamide or dimethylsulphoxide, and optionally using a catalyst such as TiCl$_4$ at a temperature range of 100° to 150°. Alternatively the amidine can be converted into the corresponding amide of formula (III) (Q is OH) by alkaline hydrolysis.

Thioamides of formula (III) (Q is SH), iminothioethers, iminoethers or iminohalides, or other derivatives containing active Q radicals as specified above, tend to be more reactive towards the amine R$^5$H and can usually be reacted without the necessity for the presence of TiCl$_4$, but otherwise employing the same conditions of temperature and solvent.

In reaction (b) compounds of formula (IV) are ring-closed by employing, for example, the same conditions in terms of catalyst and solvent as those described above for reaction (a) and preferably at a temperture of 150° C. to 200° C. The compounds of formula (IV) are conveniently prepared in situ without isolation.

When the compound prepared by reaction (a) or (b) is one in which R$^6$ or R$^9$ is hydrogen, it may be further reacted to provide other compounds of the invention. For example when R$^6$ is hydrogen, the compound can be reacted with R$^6$X by conventional alkylation or acylation type methods, X being a leaving group. The compound is dissolved in a suitable inert polar solvent such as ethanol and the reagent of formula R$^6$X added, the reaction mixture then being heated under reflux in the presence of a base. The group X can be a suitable reactive atom such a chlorine, bromine or iodine, or a reactive group such as tosyl or mesyl. Similarly, when R$^9$ is hydrogen, the compound can be reacted with a reagent of formula R$^9$X in an inert solvent and in the presence of a base.

When the compound prepared by reaction (a) or (b) is one in which n is o, it may be oxidised to provide other compounds of the invention, that is, the corresponding compound in which n is 1. Suitable oxidising agents include for example m-chloroperbenzoic acid and the reaction is preferably carried out in an inert solvent such as for example dichloromethane at a temperature of from $-10°$ C. to $+10°$ C.

The compounds of formula (I) produced by the above processes may be isolated per se or may be converted to their corresponding acid addition salts using conventional methods.

The amides of formula (III) (Q is OH) can be prepared by a process which involves the ring-closure of an amino-ester of formula (V)

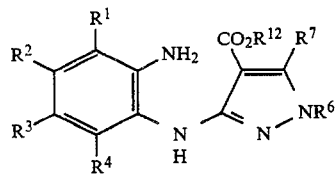

where R$^{12}$ is a C$_{1-4}$ alkyl group, employing for example sodium methylsulphinyl methanide in a suitable solvent such a dimethyl sulphoxide.

Alternatively amides of formula (III) (Q is OH) can be prepared by ring-closure of an amino-acid of formula (VI)

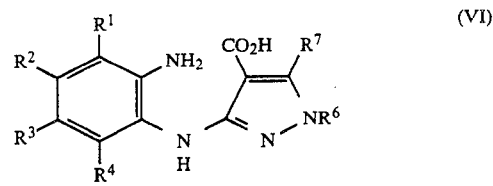

employing for example dicyclohexylcarbodiimide (DCC) in a suitable solvent such as tetrahydrofuran. These amino-acids can be obtained from the esters of formula (V) by basic hydrolysis using for example sodium hydroxide in ethanol.

The esters of formula (V) can be prepared by condensation of a pyrazole compound of formula

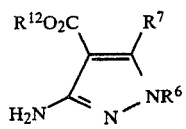

with an ortho-halonitrobenzene of formula

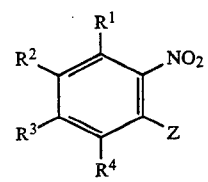

where Z is halogen, preferably fluorine, chlorine or bromine, in the presence of a base for example, sodium hydride in a solvent such as tetrahydrofuran or dimethylformamide, n-butyl lithium in tetrahydrofuran, potassium carbonate in dimethylsulphoxide or with a tetralkylammonium salt in a two-phase system, to form a nitro ester of formula

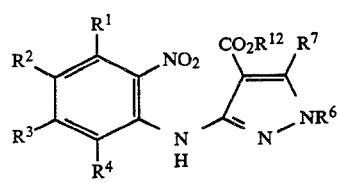

which can be reduced to the amino ester of formula (V) catalytically, employing for instance hydrogen and palladium or chemically, employing for example, stannous chloride and hydrogen chloride in aqueous ethanol, or ammonium polysulphide.

Similarly, the amidines of formula (III) (Q is NH$_2$) can be prepared by condensation of a pyrazole of formula

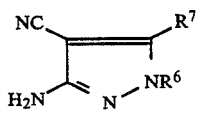

with an ortho-halonitrobenzene as outlined above, followed by simultaneous reduction and ring-closure to the amidine of formula (III) employing for example stannous chloride and hydrogen chloride in aqueous ethanol or, alternatively, by reduction with hydrogen and palladium or ammonium polysulphide followed by acid-catalysed ring closure.

Pyrazole starting materials used in the processes described above are either known compounds, see for example J. Am. Chem. Soc. (1956) 78 784; Helv. Chim. Acta (1958) 41 1052; Helv. Chim. Acta (1959) 42 349 and 763; German Pat. No. 1,106,330 and British Pat. No. 884,851; or can be prepared by conventional techniques from known compounds. The ortho-halonitrobenzene intermediates are either commercially available or can be simply prepared from commercially available substances.

Thioamides of formula (III) (Q is SH) can be prepared by treating a solution of the corresponding amide in an anhydrous basic solvent such as for example pyridine with phosphorus pentasulphide. Similarly, the amides can be converted to iminothioethers, iminoethers or iminohalides, or other derivatives containing active Q radicals, by treatment with conventional reagents such as for example in the case of an iminochloride, phosphorus pentachloride.

Compounds of formula (III) are novel and, in particular, those in which Q is hydroxyl, thiol or amino are included as an aspect of the invention.

In reaction (b), the compounds of formula (IV) are novel and they are included as a further aspect of this invention. They can be prepared in situ without isolation by reacting a compound of formula (V) with an amine of formula $R^5H$ such as by heating to a temperature between 30° C. and 120° C., for example 100° C., in a suitable solvent such as for example anisole and employing $TiCl_4$ as catalyst, or by conventional methods from compounds of formula (V) or (VI).

It will be understood that electrophilic substitution on the aromatic nucleus can be carried out on compounds of formulae (I), (III) or (IV) in conventional manner to produce other derivatives. For instance, an amide of formula (III) can be acetylated using acetyl chloride and stannic chloride or halogenated employing for example N-chlorosuccinimide, to give the corresponding acetyl or chloro derivatives. Products of formula (I) in which $R_1$, $R^2$, $R^3$ or $R^4$ is amino can be acylated or alkylated in conventional manner to form the corresponding acylamino or alkylamino derivatives.

As an illustration of the preparation of representative compounds of the invention the following reaction scheme is given, in which various routes for preparing a 4-(4-alkyl-1-piperazinyl)-2,10-dihydropyrazolo[3,4-b][1,5]benzodiazepine are shown:

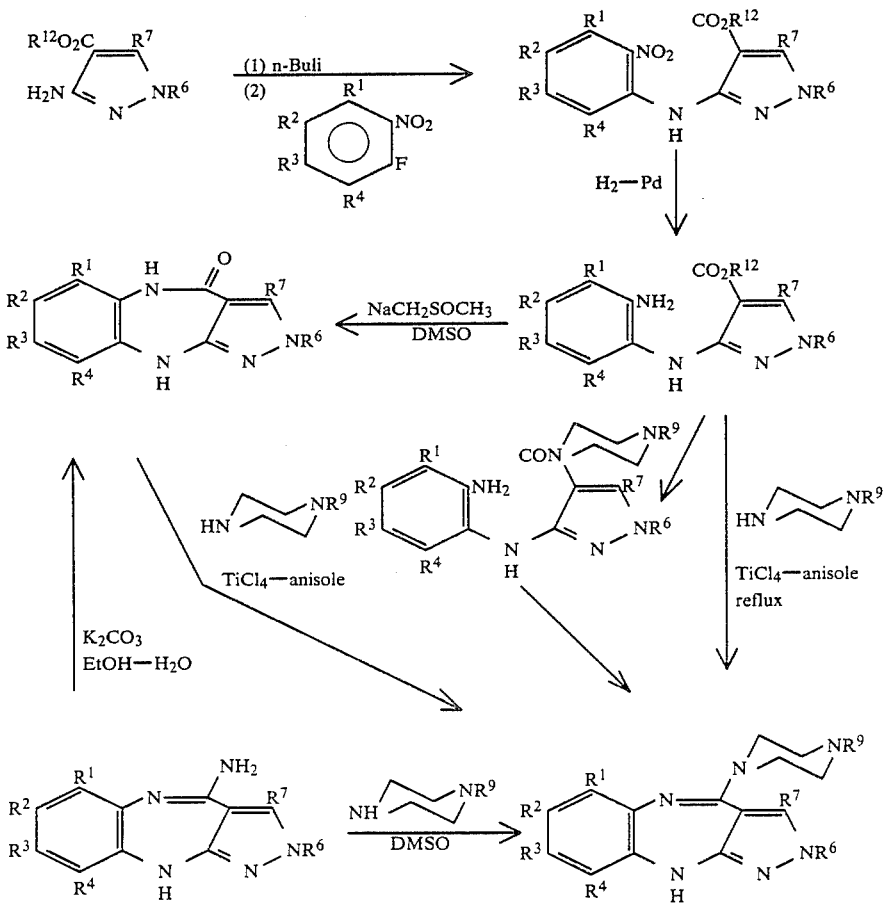

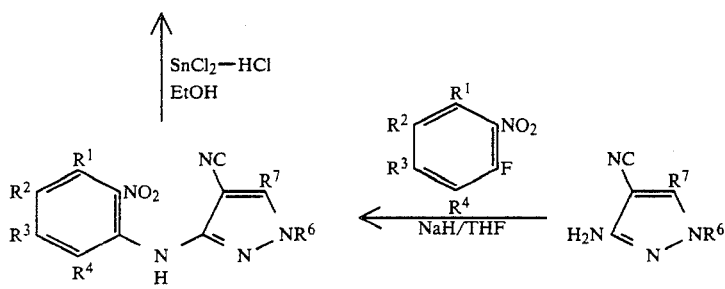

The compounds of the invention have useful central nervous system activity as demonstrated by well-known test procedures. In behavioural studies in mice, for instance, the compounds of the invention described in the following Examples were observed to produce hypothermia and activity decrease at a dose range of 12.5 to 200 mg/kg p.o. Preferred compounds have also been tested following chronic administration when a behavioural supersensitivity is produced to locally injected dopamine in a manner similar to that described in Psychopharmacologia (1975) 45 151–155. The activity profile observed in this test along with the lack of response in tests such as the production of catalepsy indicate that these compounds possess useful central nervous system activity and do not produce certain undesirable side effects. For some time it has been recognised that conventional central nervous system drugs can have undesirable characteristics and the potential absence of these side effects in compounds according to the invention represents a significant advance. In addition, compounds of the invention possess unexpected anxiolytic activity as demonstrated by their profile in the test described in Neuropharmacology (1979) 18 689–695. The compounds of formula (I) and acid addition salts thereof are thus, potent centrally acting compounds with neuroleptic, sedative, relaxant, anxiolytic or anti-emetic properties. These properties, coupled with their low toxicity render them useful in the treatment of mild anxiety states and certain kinds of psychotic conditions such a schizophrenia and acute mania.

The compounds of this invention are effective over a wide dosage range, the actual dose administered being dependent on such factors as the particular compound being used, the condition being treated and the type and size of mammal being treated. However, the dosage required will normally fall within the range of 0.5 to 50 mg/kg per day, for example in the treatment of adult humans, dosages of from 5 to 500 mg per day may be used.

The compounds of the invention will normally be administered orally or by injection and, for this purpose, the compounds will usually be utilised in the form of a pharmaceutical composition. Such compositions are prepared in a manner well known in the pharmaceutical art and comprise at least one active compound. Accordingly the invention includes a pharmaceutical composition comprising as active ingredient a compound of formula I or an acid addition salt thereof, associated with a pharmaceutically acceptable carrier. In making the compositions of the invention, the active ingredient will usually be mixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Some examples of suitable carriers are lactose, dextrose, sucrose, sorbitol, mannitol, starches, gum acacia, calcium phosphate, alginates, tragacanth, gelatin, syrup, methyl cellulose, methyland propyl-hydroxybenzoate, talc, magnesium stearate or mineral oil. The compositions of the invention may, if desired, be formulated so as to provide quick, sustained or delayed release of the active ingredient after administration to the patient.

Depending on the route of administration, the foregoing compositions may be formulated as tablets, capsules or suspensions for oral use and injection solutions for parenteral use or as suppositories. Preferably the compositions are formulated in a dosage unit form, each dosage containing from 1 to 200 mg, more usually 5 to 100 mg, of the active ingredient.

The following Examples illustrate the invention:

EXAMPLE 1

Ethyl 3-(4-fluoro-2-nitroanilino)-1-methylpyrazole-4-carboxylate

A solution of ethyl 3-amino-1-methylpyrazole-4-carboxylate (Helv. Chim. Acta (1959) 42 349)(17 g) in dry tetrahydrofuran (250 ml) was stirred under nitrogen at −10° C. n-Butyl lithium (75 ml of 1.84 molar solution in hexane) was added at −10° to −15° C. The mixture was stirred at −15° C. for 10 minutes and a solution of 2,5-difluoronitrobenzene (16 g) in dry tetrahydrofuran (50 ml) was added at −15° to −10° C. The solution was warmed to room temperature and stirred for 1 hour. The ink-blue solution was poured into 500 ml of a 1:1 mixture of hydrochloric acid (2M) and ice-brine, extracted with chloroform (3×250 ml), washed with water (2×250 ml), dried with magnesium sulphate and evaporated to dryness. The brick-red residue was crystallised from ethanol (800 ml) to give the title compound having a m.p. of 162° C.

The following compounds were similarly prepared using the above process. In each case the recrystallisation solvent is given in parenthesis.

Ethyl 1-methyl-3-(4,5-difluoro-2-nitroanilino)pyrazole-4-carboxylate, m.p. 141° C. (isopropanol)

Ethyl 1-ethyl-3-(4-fluoro-2-nitroanilino)pyrazole-4-carboxylate, m.p. 136° C. (ethanol).

Ethyl 1-methyl-3-(2-nitro-4-trifluoromethylanilino)-pyrazole-4-carboxylate, m.p. 158° C. (isopropanol).

Ethyl 3-(5-fluoro-2-nitroanilino)-1-methylpyrazole-4-carboxylate, m.p. 165° C. (ethanol).

Ethyl 3-(4-fluoro-2-nitroanilino)-1-(1-propyl)pyrazole-4-carboxylate, m.p. 109° C. (ethanol).

Ethyl 3-(4-fluoro-2-nitroanilino)-1-(1-methylethyl)-pyrazole-4-carboxylate, m.p. 106.5° C. (ethanol).

Ethyl 3-(4-fluoro-2-nitroanilino)-1-(1-hexyl)pyrazole-4-carboxylate, m.p. 73° C. (ethanol).

Ethyl 3-(2-nitroanilino)-1-methylpyrazole-4-carboxylate, m.p. 146° C. (isopropanol).

EXAMPLE 2

3-(4-Chloro-2-nitroanilino)-1-methylpyrazole-4-carbonitrile

3-Amino-1-methylpyrazole-4-carbonitrile (Helv. Chim. Acta (1959) 42 763) (3.66 g) was stirred in dry tetrahydrofuran (40 ml). Sodium hydride (50% oil dispersion, 2.28 g) was added and the mixture was stirred for 10 minutes. 2,5-Dichloronitrobenzene (5.76 g) was added and the solution stirred under nitrogen for 20 hours. Water was added dropwise to destroy any excess sodium hydride, then the solution was poured on to a mixture of ice and dilute hydrochloric acid. After standing for 1 hour the brick-red precipitate was filtered, washed with water and dried. Crystallisation from ethanol-ethyl acetate afforded the product m.p. 205° C.

The following compounds were similarly prepared. In each case the recrystallisation solvent is given in parenthesis.

3-(4-Iodo-2-nitroanilino)-1-methylpyrazole-4-carbonitrile, m.p. 212° C. (ethanol-ethyl acetate)

3-(5-Chloro-2-nitroanilino)-1-methylpyrazole-4-carbonitrile, m.p. 187° C. (ethanol-ethyl acetate)

3-(4,5-Dichloro-2-nitroanilino)-1-methylpyrazole-4-carbonitrile, m.p. 225° C. (ethanol-ethyl acetate)

3-(4-Bromo-2-nitroanilino)-1-methylpyrazole-4-carbonitrile, m.p. 208° C. (ethanol-ethyl acetate)

3-(4-Trifluoromethyl-2-nitroanilino)-1-methylpyrazole-4-carbonitrile, m.p. 183° C.–184° C. (ethanol)

3-(4-Chloro-2-nitroanilino)-1-ethylpyrazole-4-carbonitrile, m.p. 172° C. (ethanol-ethylacetate)

3-(4-Chloro-2-nitroanilino)-1-(2-methyl-1-propyl)-pyrazole-4-carbonitrile, m.p. 151° C. (ethanol)

3-(4-Chloro-2-nitroanilino)-1-cyclopentylpyrazole-4-carbonitrile, m.p. 145° C. (ethanol)

3-(4-Fluoro-2-nitroanilino)-1-methylpyrazole-4-carbonitrile, m.p. 174° C. (ethanol)

3-(3-Chloro-2-nitroanilino)-1-methylpyrazole-4-carbonitrile, m.p. 190° C. (ethanol)

1-Methyl-3-(2,4-dinitroanilino)pyrazole-4-carbonitrile, m.p. 224° C. (ethanol-ethyl acetate)

EXAMPLE 3

Ethyl 1,5-dimethyl-3-(4-fluoro-2-nitroanilino)pyrazole-4-carboxylate

Ethyl 3-amino-1,5-dimethylpyrazole-4-carboxylate (5.5 g), 2,5-difluoronitrobenzene (6.6 g) and anhydrous potassium carbonate (8.9 g), were stirred in dimethylsulphoxide (60 ml) under dry nitrogen at 70° C. for 20 hours. The mixture was poured on to 300 ml of ice-cold dilute hydrochloric acid, extracted with chloroform (3×), washed with water (2×), dried with magnesium sulphate and the solvent evaporated under reduced pressure. The yellow-brown residue was crystallized from ethanol to give the title compound having a m.p. of 174° C.

EXAMPLE 4

1-Methyl-3-(2-nitroanilino)pyrazole-4-carbonitrile

3-Amino-1-methylpyrazole-4-carbonitrile (Helv. Chim. Acta (1959) 42, 763) (7.5 g) and 2-fluoronitrobenzene (8.4 g) were stirred in toluene (120 ml) with Adogen 464 (3.0 g) and potassium carbonate (16.5 g) at 60° C. 50% Sodium hydroxide solution (0.1 ml) was added and the mixture was heated under reflux for 2 hours. The mixture was poured on to dilute hydrochloric acid, extracted, the aqueous layer washed with toluene and the combined extracts washed twice with water. After evaporation the residue was crystallised from ethanol (750 ml) to give the title compound, m.p. 172° C.

EXAMPLE 5

Ethyl 3-(2-amino-4-trifluoromethylanilino)-1-methylpyrazole-4-carboxylate

Ethyl 1-methyl-3-(2-nitro-4-trifluoromethylanilino)-pyrazole-4-carboxylate (9.2 g) was hydrogenated at 60 p.s.i. in a mixture of ethyl acetate (200 ml) and ethanol (50 ml) over 10% palladium on charcoal (1.0 g). The catalyst was removed by filtration, the solvent evaporated and the residue crystallised from carbon tetrachloride to give the title compound m.p. 162° C.

The following compounds were similarly prepared and used in Examples 10 and 13 without purification.

Ethyl 3-(2-amino-4-fluoroanilino)-1-methylpyrazole-4-carboxylate.

Ethyl 3-(2-amino-4-fluoroanilino)-1,5-dimethylpyrazole-4-carboxylate.

Ethyl 3-(2-amino-4-fluoroanilino)-1-ethylpyrazole-4-carboxylate.

Ethyl 3-(2-amino-5-fluoroanilino)-1-methylpyrazole-4-carboxylate.

Ethyl 3-(2-amino-4,5-difluoroanilino)-1-methylpyrazole-4-carboxylate.

Ethyl 3-(2-amino-4-fluoroanilino)-1-(1-propyl)pyrazole-4-carboxylate.

Ethyl 3-(2-amino-4-fluoroanilino)-1-(1-methylethyl)pyrazole-4-carboxylate.

Ethyl 3-(2-amino-4-fluoroanilino)-1-(1-hexyl)pyrazole-4-carboxylate.

Ethyl 3-(2-aminoanilino)-1-methylpyrazole-4-carboxylate.

EXAMPLE 6

3-(2-Amino-4-nitroanilino)-1-methylpyrazole-4-carbonitrile

1-Methyl-3-(2,4-dinitroanilino)pyrazole-4-carbonitrile (2.88 g) was stirred in a mixture of 0.88 ammonia solution (60 ml), water (90 ml) and ethanol (60 ml) under reflux whilst a slow stream of hydrogen sulphide gas was bubbled through for 2 hours. The mixture was cooled, filtered and the residue crystallised from ethyl acetate-n-hexane to give the title compound m.p. 204° C.

EXAMPLE 7

4-Methyl-1-(3-[2-amino-4-trifluoromethylanilino]-1-methylpyrazole-4-carbonyl)piperazine Ethyl 3-(2-amino-4-trifluoromethylanilino)-1-methyl-pyrazole-4-carboxylate (4.75 g) was stirred in a mixture of N-methylpiperazine (25 ml) and anisole (65 ml). A solution of titanium tetrachloride (4.2 ml) in anisole (20 ml) was added and the mixture was stirred under nitrogen at 65° C. for 30 minutes. A mixture of isopropanol (25 ml) and 0.88 ammonia solution (25 ml) was added and the stirred mixture cooled to 25° C. The precipitate was removed by filtration, washing with ethyl acetate. The combined filtrates were washed with water (3X), dried over magnesium sulphate, the solvent evaporated and the residue crystallised from acetonitrile to give the title compound m.p. 170° C.

Other examples of this type were prepared in situ and cyclised as in Example 13.

EXAMPLE 8

4-Amino-7-chloro-2,10-dihydro-2-methyl-pyrazolo[3,4-b][1,5]benzodiazepine

To 1-methyl-3-(4-chloro-2-nitroanilino)pyrazole-4-carbonitrile (16 g) stirred in ethanol (500 ml) was added a solution of anhydrous stannous chloride (33.1 g) in concentrated hydrochloric acid (176 ml). The mixture was heated under reflux for 2 hours, cooled, filtered and crystallised from methylated spirits (1 liter) to give the title compound as its hydrochloride salt m.p. >260° C. 2.0 g of the hydrochloride salt was partitioned between dilute ammonia solution and chloroform. The organic phase was washed with water, dried with magnesium sulphate, evaporated and the residue crystallised from chloroform-n-hexane to give the title compound as the free base m.p. 240° C.

The following compounds were similarly prepared and used as the hydrochlorides without purification in Example 15.

4-Amino-2,10-dihydro-7-iodo-2-methylpyrazolo[3,4-b][1,5]benzodiazepine

4-Amino-8-chloro-2,10-dihydro-2-methylpyrazolo[3,4-b][1,5]benzodiazepine

4-Amino-7,8-dichloro-2,10-dihydro-2-methyl-pyrazolo[3,4-b][1,5]benzodiazepine

4-Amino-7-bromo-2,10-dihydro-2-methylpyrazolo[3,4-b][1,5]benzodiazepine

4-Amino-2,10-dihydro-7-trifluoromethyl-2-methylpyrazolo[3,4-b][1,5]benzodiazepine 4-Amino-7-chloro-2-ethyl-2,10-dihydropyrazolo[3,4-b][1,5]benzodiazepine 4-Amino-7-chloro-2,10-dihydro-2-(2-methyl-1-propyl)-pyrazolo[3,4-b][1,5]benzodiazepine 4-Amino-7-chloro-2-cyclopentyl-2,10-dihydropyrazolo[3,4-b][1,5]benzodiazepine 4-Amino-7-fluoro-2,10-dihydro-2-methylpyrazolo[3,4-b][1,5]benzodiazepine 4-Amino-6-chloro-2,10-dihydro-2-methylpyrazolo[3,4-b][1,5]benzodiazepine

EXAMPLE 9

4-Amino-2,10-dihydro-2-methyl-7-nitropyrazolo[3,4-b][1,5]benzodiazepine hydrochloride 3-(2-Amino-4-nitroanilino)-1-methylpyrazole-4-carbonitrile (250 mg) was heated under reflux in a mixture of isopropanol (10 ml) and concentrated hydrochloric acid (1 ml) for 20 hours. The solution was evaporated under reduced pressure and the residue crystallised from methylated spirits to give the title compound m.p. >260°.

EXAMPLE 10

7-Fluoro-2-methyl-2,4,5,10-tetrahydropyrazolo[3,4-b][1,5]benzodiazepin-4-one

A solution of sodium methyl sulphinyl methanide was generated by stirring sodium hydride (50% oil dispersion, 1.5 g) in dry dimethylsulphoxide (15 ml) at 65° C. until gas evolution ceased. A solution of ethyl 3-(2-amino-4-fluoroanilino)-1-methylpyrazole-4-carboxylate (2.7 g) dissolved in dry dimethyl sulphoxide (5 ml) was added dropwise and the mixture stirred at 65° C. for 20 minutes. The mixture was poured on to excess ice-water, filtered and dried to give the title compound which was crystallised from chloroform-hexane m.p. 264° C.

EXAMPLE 11

7-Chloro-2,4,5,10-tetrahydro-2-methylpyrazolo[3,4-b][1,5]benzodiazepin-4-one

4-Amino-7-chloro-2,10-dihydro-2-methyl-pyrazolo[3,4-b][1,5]benzodiazepine hydrochloride (11.3 g) and potassium carbonate (16.8 g) were heated under reflux in a mixture of ethanol (200 ml) and water (20 ml) for 48 hours. Water (300 ml) was added and the solution cooled. The precipitate was crystallised from acetic acid to give the title compound m.p. >260° C.

EXAMPLE 12

7-Chloro-2,4,5,10-tetrahydro-2-methylpyrazolo[3,4-b][1,5]benzodiazepine-4-thione 7-Chloro-2,4,5,10-tetrahydro-2-methyl-pyrazolo[3,4,b][1,5]benzodiazepine-4-one (7.2 g) was added to a stirred solution of phosphorous pentasulphide (6.5 g) in anhydrous pyridine (145 ml). The mixture was heated under reflux for 1.5 hours, poured on to ice, and the precipitate crystallised from chloroform methanol to yield the title compound m.p. >260° C.

EXAMPLE 13

2-Ethyl-7-fluoro-2,10-dihydro-4-(4-methyl-1-piperazinyl)pyrazolo[3,4-b][1,5]benzodiazepine Ethyl 3-(2-amino-4-fluoroanilino)-1-ethylpyrazole-4-carboxylate (2.64 g) was dissolved in a mixture of N-methyl piperazine (12.5 ml.) and anisole (50 ml). Titanium tetrachloride (3 ml) in anisole (12 ml) was added, dropwise, and the stirred solution was heated at reflux under an atmosphere of dry nitrogen for 24 hours. The mixture was cooled to 60° C. and a mixture of isopropanol (10 ml) and 0.88 ammonia solution (10 ml) cautiously added. This mixture was allowed to cool to room temperature over 1 hour, then filtered through a pad of Celite, whilst washing with ethyl acetate. The filtrate was washed with water (3×), dried over magnesium sulphate and the solvent removed. The residue was filtered through a short column of Florisil, eluting with ethyl acetate. After removal of solvent the title product was crystallised from acetonitrile m.p. 181° C.

The following compounds were similarly prepared:

7-Fluoro-2,10-dihydro-2,3-dimethyl-4-(4-methyl-1-piperazinyl)pyrazolo[3,4-b][1,5]benzodiazepine, m.p. 234° C. (acetonitrile)

7-Chloro-2,10-dihydro-2-methyl-4-(4-methyl-1-piperazinyl)pyrazolo[3,4-b][1,5]benzodiazepine, m.p. 107°-109° C. (acetonitrile)

8-Fluoro-2,10-dihydro-2-methyl-4-(4-methyl-1-piperazinyl)pyrazolo[3,4-b][1,5]benzodiazepine, m.p. 192° C. (acetonitrile)

7,8-Difluoro-2,10-dihydro-2-methyl-4-(4-methyl-1-piperazinyl)pyrazolo[3,4-b][1,5]benzodiazepine, m.p. 214° C. (acetonitrile).

7-Fluoro-2,10-dihydro-4-(4-methyl-1-piperazinyl)-2-(1-propyl)pyrazolo[3,4-b][1,5]benzodiazepine, m.p. 146° C. (acetonitrile).

7-Fluoro-2,10-dihydro-2-(1-methylethyl)-4-(4-methyl-1-piperazinyl)pyrazolo[3,4-b][1,5]benzodiazepine, m.p. 74°-76° C. (cyclohexane-n-hexane)

7-Fluoro-2-(1-hexyl)-2,10-dihydro-4-(4-methyl-1-piperazinyl)pyrazolo[3,4-b][1,5]benzodiazepine, m.p. 99° C. (cyclohexane-n-hexane).

2,10-Dihydro-2-methyl-4-(4-methyl-1-piperazinyl)-pyrazolo[3,4-b][1,5]benzodiazepine, m.p. 212° C. (acetonitrile)

EXAMPLE 14

7-Fluoro-2,10-dihydro-2-methyl-4-(4-methyl-1-piperazinyl)pyrazolo[3,4-b][1,5]benzodiazepine and citrate salt 7-Fluoro-2,4,5,10-tetrahydro-2-methylpyrazolo[3,4-b][1,5] benzodiazepin-4-one (0.95 g) was stirred in a mixture of N-methylpiperazine (10 ml) and anisole (15 ml). A solution of titanium tetrachloride (0.55 ml) in anisole (10 ml) was added and the mixture stirred under nitrogen at 130° C. for 2 hours, poured on to ice-dilute ammonia solution and extracted into methylene chloride. The extract was washed with water (3×), dried and evaporated. The residue was chromatographed on Florisil eluting with ethyl acetate and crystallised from acetonitrile, m.p. 192° C. The citrate salt was prepared by adding a solution of citric acid in ethanol to a solution of the title compound in a 1:1 mixture of ethanol and ethyl acetate m.p. 138° C. (softens)

EXAMPLE 15

2,10-Dihydro-7-iodo-2-methyl-4-(4-methyl-1-piperazinyl)pyrazolo[3,4-b][1,5]benzodiazepine To a mixture of N-methylpiperazine (10 ml), dimethylsulphoxide (25 ml) and toluene (25 ml) through which nitrogen had been bubbled for 30 minutes was added 4-amino-2,10-dihydro-7-iodo-2-methylpyrazolo[3,4-b][1,5]benzodiazepine hydrochloride (3.84 g). The stirred mixture was heated under nitrogen at 120° C. for 20 hours. The mixture was cooled to 60° C. and water (25 ml) added. The residue was filtered, dried and crystallised from chloroform-n-hexane m.p. 113° C. The following compounds were similarly prepared:

8-Chloro-2,10-dihydro-2-methyl-4-(4-methyl-1-piperazinyl)pyrazolo[3,4-b][1,5]benzodiazepine, m.p. 221° C. (chloroform-n-hexane).

7,8-Dichloro-2,10-dihydro-2-methyl-4-(4-methyl-1-piperazinyl)pyrazolo[3,4-b][1,5]benzodiazepine, m.p. 158° C. (acetonitrile)

7-Bromo-2,10-dihydro-2-methyl-4-(4-methyl-1-piperazinyl)pyrazolo[3,4-b][1,5]benzodiazepine, m.p. 162° C. (acetonitrile)

2,10-Dihydro-7-trifluoromethyl-2-methyl-4-(4-methyl-1-piperazinyl)pyrazolo[3,4-b][1,5]benzodiazepine, m.p. 129°–130° C. (ethyl acetate-hexane)

7-Chloro-2-ethyl-2,10-dihydro-4-(4-methyl-1-piperazinyl)pyrazolo[3,4-b][1,5]benzodiazepine, m.p. 165° C. (acetonitrile)

7-Chloro-2,10-dihydro-4-(4-methyl-1-piperazinyl)-2-(2-methyl-1-propyl)pyrazolo[3,4-b][1,5]benzodiazepine, m.p. 161° C. (acetonitrile)

7-Chloro-2-cyclopentyl-2,10-dihydro-4-(4-methyl-1-piperazinyl)pyrazolo[3,4-b][1,5]benzodiazepine, m.p. 151° C. (acetonitrile)

7-Fluoro-2,10-dihydro-2-methyl-4-(1-piperazinyl)-pyrazolo[3,4-b][1,5]benzodiazepine, m.p. 183°–185° C. (acetonitrile)

6-Chloro-2,10-dihydro-2-methyl-4-(4-methyl-1-piperazinyl)[3,4-b][1,5]benzodiazepine, m.p. 214° C. (chloroform-n-hexane)

EXAMPLE 16

7-Chloro-2,10-dihydro-2-methyl-4-(4-methyl-1-piperazinyl)pyrazolo[3,4-b][1,5]benzodiazepine 7-Chloro-2,4,5,10-tetrahydro-2-methyl-4-(4-methyl-1-piperazinyl)pyrazolo[3,4-b][1,5]benzodiazepin-4-thione (0.265 g) was heated under reflux in N-methylpiperazine (3 ml) for 20 hours. The cooled mixture was dissolved in 1M hydrochloric acid, washed with ethyl acetate (2×), basified with 0.88 ammonia and extracted into dichloromethane. The extract was washed with water, dried with magnesium sulphate and evaporated to leave a residue which was crystallised from chloroform-n-hexane m.p. 173°–176° C.

EXAMPLE 17

4-(4-Cyclopropylmethyl-1-piperazinyl)-7-fluoro-2-methyl-2,10-dihydropyrazolo[3,4-b][1,5]benzodiazepine A solution of 7-fluoro-2,10-dihydro-2-methyl-4-(1-piperazinyl)pyrazolo[3,4-b][1,5]benzodiazepine (1.0 g), bromomethylcyclopropane (0.5 g) and triethylamine (0.0375 g) in acetonitrile (30 ml) was stirred at ambient temperature for 20 hours. The solution was poured into water and the product extracted with chloroform (3×). The organic extract was washed with saturated brine and water, dried over magnesium sulphate, the solvent removed and the residue crystallised from ethyl acetate to give the title compound m.p. 188°–189° C. 4-(4-Benzyl-1-piperazinyl)-7-fluoro-2,10-dihydro-2-methyl-pyrazolo[3,4-b][1,5]benzodiazepine was similarly prepared, m.p. 241°–245° C. (ethyl acetate-diethyl ether).

EXAMPLE 18

4-(7-Fluoro-2,10-dihydro-2-methyl-pyrazolo[3,4-b][1,5]benzodiazepin-4-yl)-1-methyl piperazine-1-oxide monohydrate 7-Fluoro-2,10-dihydro-2-methyl-4-(4-methyl-1-piperazinyl)-pyrazolo[3,4-b][1,5]benzodiazepine (2.0 g) was stirred in dichloromethane (50 ml) at 0°–5° C. whilst m-chloroperbenzoic acid (1.5 g) was added in portions. The solution was stirred for 30 minutes then filtered through a column of basic alumina, eluting with 9:1 chloroform:methanol to give, after removal of the solvent and crystallisation from acetonitrile-diethyl ether, the title compound m.p. 228°.

The following formulations were prepared employing 7-fluoro-2,10-dihydro-2-methyl-4-(4-methyl-1-piperazinyl)pyrazolo[3,4-b][1,5]benzodiazepine as the active ingredient. Formulations containing other active ingredients of the invention can be prepared in a similar manner.

EXAMPLE 19

Tablets each containg 10 mg of active ingredient were made up as follows

| | |
|---|---|
| Active ingredient | 10 mg |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |

| | |
|---|---|
| -continued | |
| Total | 100 mg |

The active ingredient, starch and cellulose were passed through a No. 44 mesh B.S. sieve and mixed thoroughly. The solution of polyvinylpyrrolidone was mixed with the resultant powders which were then passed through a No. 12 mesh B.S. sieve. The granules so produced were dried at 50°–60° C. and passed through a No. 16 mesh B.S. sieve. The sodium carboxymethyl starch, magnesium stearate and talc, previously passed through a No. 60 mesh B.S. sieve, were then added to the granules which, after mixing, were compressed on a tablet machine to yield tablets each weighting 100 mg.

EXAMPLE 20

Capsules each containing 20 mg of medicament were made as follows

| | |
|---|---|
| Active ingredient | 20 mg |
| Starch | 89 mg |
| Microcrystalline cellulose | 89 mg |
| Magnesium stearate | 2 mg |
| Total | 200 mg |

The active ingredient, cellulose, starch and magnesium stearate were passed through a No. 44 mesh B.S. sieve and filled into hard gelatin capsules in 200 mg quantities.

EXAMPLE 21

Suppositories each containing 25 mg of active ingredient were made as follows

| | |
|---|---|
| Medicament | 25 mg |
| Saturated fatty acid glycerides to | 2,000 mg |

The active ingredient was passed through a No. 60 mesh B.S. sieve and suspended in the saturated fatty acid glycerides previously melted using the minimum heat necessary. The mixture was then poured into a suppository mould of nominal 2 g capacity and allowed to cool.

EXAMPLE 22

Suspensions each containing 5 mg of medicament per 5 ml dose were made as follows

| | |
|---|---|
| Medicament | 5 mg |
| Sodium carboxymethyl cellulose | 50 mg |
| Syrup | 1.25 ml |
| Benzoic acid solution | 0.10 ml |
| Flavour | q.s. |
| Colour | q.s. |
| Purified water to | 5 ml |

The medicament was passed through a No. 44 mesh B.S. sieve and mixed with the sodium carboxymethylcellulose and syrup to form a smooth paste. The benzoic acid solution, flavour and colour were diluted with some of the water and added, with stirring. Sufficient water was then added to produce the required volume.

We claim:

1. An intermediate compound of the formula

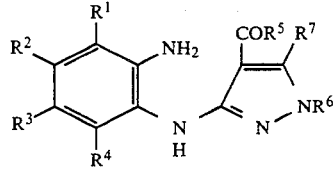

where $R^1$, $R^2$, and $R^3$ independently represent hydrogen, halogen, or $C_{1-4}$ haloalkyl $R^4$ is hydrogen;

in which $R^5$ is a group of the formula

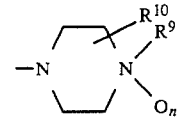

where $R^9$ is hydrogen, $C_{1-4}$ alkyl, $C_{3-7}$ cycloalkyl $C_{1-4}$ alkyl, or benzyl, where $R^{10}$ is hydrogen, and where n is 0;

in which $R^6$ is $C_{1-6}$alkyl, $C_{3-7}$ cycloalkyl, or $C_{3-7}$ cycloalkyl $C_{1-4}$ alkyl, and in which $R^7$ is hydrogen.

* * * * *